(12) United States Patent
Schapiro et al.

(10) Patent No.: US 9,387,969 B2
(45) Date of Patent: Jul. 12, 2016

(54) TOOTHPASTE COMPOSITION AND METHOD OF APPLYING A SINGLE SERVING OF TOOTHPASTE TO A TOOTHBRUSH

(71) Applicants: Edward Schapiro, Boca Raton, FL (US); Daniel M. Schapiro, Boca Raton, FL (US); Michelle Bacarella, Gilbert, AZ (US); Tom Ingolia, Morton, IL (US); Steve Rittmanic, Chandler, AZ (US)

(72) Inventors: Edward Schapiro, Boca Raton, FL (US); Daniel M. Schapiro, Boca Raton, FL (US); Michelle Bacarella, Gilbert, AZ (US); Tom Ingolia, Morton, IL (US); Steve Rittmanic, Chandler, AZ (US)

( * ) Notice: Subject to any disclaimer, the term of this patent is extended or adjusted under 35 U.S.C. 154(b) by 642 days.

(21) Appl. No.: 13/646,241

(22) Filed: Oct. 5, 2012

(65) Prior Publication Data

US 2013/0029294 A1  Jan. 31, 2013

Related U.S. Application Data

(63) Continuation-in-part of application No. 13/447,891, filed on Apr. 16, 2012, now Pat. No. 8,967,378.

(60) Provisional application No. 61/475,297, filed on Apr. 14, 2011.

(51) Int. Cl.
| | |
|---|---|
| *A61Q 11/00* | (2006.01) |
| *A61K 8/73* | (2006.01) |
| *A61K 8/97* | (2006.01) |
| *B65D 75/32* | (2006.01) |
| *A61K 8/65* | (2006.01) |
| *A61K 8/86* | (2006.01) |

(52) U.S. Cl.
CPC ............... *B65D 75/327* (2013.01); *A61K 8/65* (2013.01); *A61K 8/73* (2013.01); *A61K 8/733* (2013.01); *A61K 8/86* (2013.01); *A61K 8/97* (2013.01); *A61Q 11/00* (2013.01); *B65D 2231/005* (2013.01)

(58) Field of Classification Search
USPC ............................... 424/49, 401, 58, 687, 485
See application file for complete search history.

(56) References Cited

U.S. PATENT DOCUMENTS

| | | | | |
|---|---|---|---|---|
| 6,485,711 | B1 * | 11/2002 | Olmstead ........................ | 424/58 |
| 2006/0086048 | A1 * | 4/2006 | Romley ......................... | 49/103 |
| 2006/0134020 | A1 * | 6/2006 | Robinson et al. ............... | 424/52 |
| 2006/0188454 | A1 * | 8/2006 | Corcoran ................. | A61K 8/25 |
| | | | | 424/49 |
| 2010/0055053 | A1 * | 3/2010 | Ripley ................... | A61K 8/365 |
| | | | | 424/49 |
| 2012/0034280 | A1 * | 2/2012 | Cohen ..................... | A61K 8/20 |
| | | | | 424/401 |

* cited by examiner

*Primary Examiner* — Lezah Roberts
(74) *Attorney, Agent, or Firm* — Robert M. Downey, P.A.

(57) ABSTRACT

A toothpaste composition includes different combinations of konjac gum and/or agar-agar, alginates, gelatin, pectin, xanthan, tara gum, gum arabic, carrageenan, celluloses, gellan gum, guar gum, inulin, konjac, locust bean gum, pectin, tragacanth, xanthan, polyethylene glycol-3350, xylitol, calcium carbonate, stevia, quillaja, liquid bioflavonoid extract, and water. The toothpaste composition produces a toothpaste product that maintains its shape prior to being used for brushing one's teeth and is preferably formed into a single serving of toothpaste stored in an open-top compartment having a removable protective film. A method of applying a single serving of toothpaste to a toothbrush includes the steps of pressing the bristles of a toothbrush against the single serving of toothpaste so that the single serving of toothpaste clings or otherwise adheres to the bristles, and subsequently pulling the toothbrush away from the compartment for brushing one's teeth.

3 Claims, 2 Drawing Sheets

TOOTHPASTE COMPOSITION AND METHOD OF APPLYING A SINGLE SERVING OF TOOTHPASTE TO A TOOTHBRUSH

This patent application is a Continuation-in-Part based on nonprovisional patent application Ser. No. 13/447,891 filed on Apr. 16, 2012 which was based on provisional patent application Ser. No. 61/475,297 filed on Apr. 14, 2011.

BACKGROUND OF THE INVENTION

1. Field of the Invention

The present invention relates to toothpaste for brushing one's teeth and, more particularly, a toothpaste composition and method of applying a single serving of toothpaste to a toothbrush.

2. Discussion of the Related Art

Toothpaste is a paste or gel used to clean and improve the health and aesthetic appearance of teeth. Used in conjunction with a toothbrush, toothpaste promotes oral hygiene by aiding the removal of dental plaque and food from the teeth, and often includes fluoride for prevention of tooth and gum disease.

Toothpaste is typically stored within a cavity of a handheld container, which may be squeezed by a user to force the toothpaste outwards through an opening in communication with the cavity. The user must continue to squeeze the handheld container until the desired amount of toothpaste has been emitted onto the user's toothbrush and the user can begin brushing his or her teeth. This process of emitting toothpaste from a tube onto a toothbrush can often result in a mess, particularly for young children who are inexperienced with the proper method for applying the proper amount of toothpaste for a single brushing session.

Therefore, there exists a need for a toothpaste composition that may be stored in single serving portions and which may be easily transferred to a toothbrush prior to brushing one's teeth.

OBJECTS AND ADVANTAGES OF THE INVENTION

Considering the foregoing, it is a primary object of the present invention to provide a toothpaste composition that maintains a preformed shape prior to use.

It is a further object of the present invention to provide a toothpaste composition that for single servings of toothpaste which can be easily picked up by pushing the bristles of a toothbrush into the preformed shape of toothpaste.

It is a further object of the present invention to provide a package for containing one or more single servings of a toothpaste composition, and wherein the packaging and single serving toothpaste composition are particularly suited for use "on-the-go" or when traveling.

It is a further of the present invention to provide a method of applying a single serving of toothpaste to a toothbrush that prevents young children from making a mess while preparing to brush their teeth.

It is a further object of the present invention to provide a method of applying a single serving of toothpaste to a toothbrush by pushing the bristles of a toothbrush into a single serving preformed shape of toothpaste so that the single serving of toothpaste clings to the bristles in a manner that is ready for brushing one's teeth.

These and other objects and advantages of the present invention are more readily apparent with reference to the detailed description and accompanying drawings.

SUMMARY OF THE INVENTION

The present invention is directed to a toothpaste composition and a method of applying a single serving of toothpaste to the bristles of a toothbrush. Several embodiments of the toothpaste composition include different combinations of konjac gum and/or agar-agar, alginates, gelatin, pectin, xanthan, tara gum, gum arabic, carrageenan, celluloses, gellan gum, guar gum, inulin, konjac, locust bean gum, pectin, tragacanth, xanthan, polyethylene glycol-3350, xylitol, calcium carbonate, stevia, quillaja, liquid bioflavonoid extract, and water. Each of the above-listed ingredients can be natural or synthetically produced. The toothpaste composition produces a toothpaste product that maintains its shape prior to being used for brushing one's teeth and is preferably formed into a single serving of toothpaste stored in an open-top compartment of a package having a removable protective film. To apply the single serving of the toothpaste composition to a toothbrush, a user presses the bristles of a toothbrush against the single serving of toothpaste, causing the single serving of toothpaste to cling to the bristles. Next, the user pulls the toothbrush away from the compartment of the dispensing package, with the single serving of toothpaste on the bristles for brushing his or her teeth.

DESCRIPTION OF THE DRAWINGS

For a fuller understanding of the nature of the present invention, reference should be made to the following detailed description taken in conjunction with the accompanying drawings in which.

Like reference numerals refer to like referenced parts throughout the several views of the drawings.

DETAILED DESCRIPTION OF THE PREFERRED EMBODIMENTS

Figure 1:
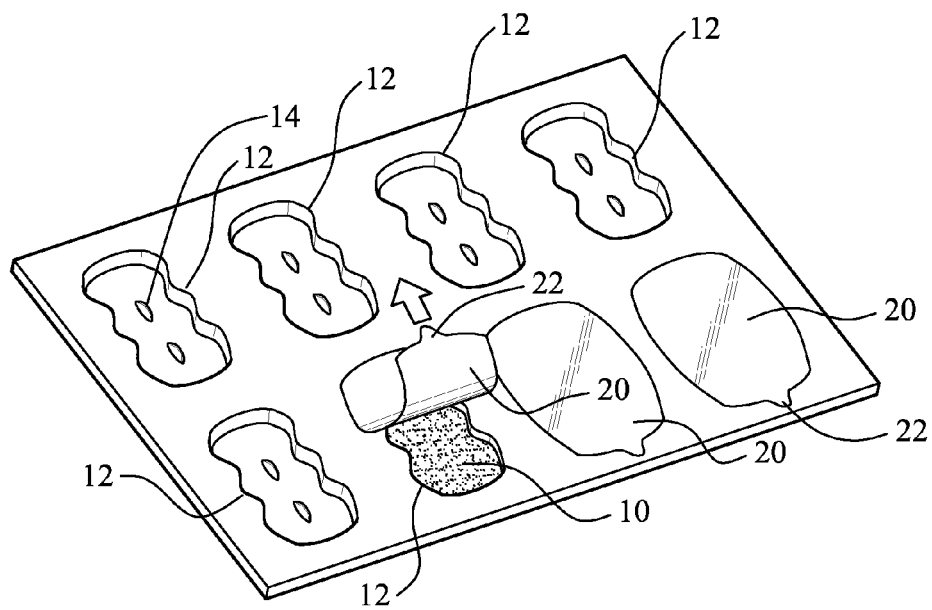
FIG. 1 is a perspective view illustrating the single servings of toothpaste in preformed shapes of the present invention stored in spaced compartments of a dispensing package having removable protective films for maintaining the single servings of toothpaste therein, in accordance with one embodiment.

Referring to the drawings, the single servings of toothpaste in preformed shapes produced by the toothpaste composition and method of applying the single serving of toothpaste to a toothbrush are shown according to the several embodiments of the invention and are generally indicated as 10. The toothpaste composition produces a toothpaste product that maintains its shape prior to being used for brushing one's teeth.

A first embodiment of a preferred toothpaste composition formulation of the single servings 10 of toothpaste in preformed shapes includes the following ingredients:

EXAMPLE 1

| Ingredient | Percentage by Weight in the Composition |
|---|---|
| Konjac | 1-3% |
| Tara Gum | 0.1-0.5% |
| Xanthan/Guar | 0.15-0.35% |
| Polyethylene glycol-3350 | 2.75-3.9% |
| Xylitol | 38-51.2% |
| Calcium Carbonate | 5.79-7.14% |
| *Stevia* | 0.01-0.45% |
| *Quillaja* | 1.02-2.1% |
| Bioflavonoid | 0.02-0.04% |
| Water | 41-54% |

A preferred process for production of the first embodiment of the single servings 10 of toothpaste in preformed shapes includes the following steps:

1. Heat water to between 100-212 degrees Fahrenheit.
2. Gradually add Xylitol to the heated water and mix until completely dissolved and a clear solution remains.
3. Cool the solution to 60-85 degrees Fahrenheit.
4. In a high shear mixer at a low speed, add Liquid Bioflavonoid and Quillaja to cooled solution and mix until completely dissolved.
5. In a ribbon-type blender at a medium speed, blend together Konjac, Tara Gum, Xanthan/Guar, and Polyethylene glycol until well blended.
6. In a shaft-type homogenizing blender at low speed or bottom-mounted liquefier, add the blended solids from Step 5 to the solution from Step 4 and mix until mostly dissolved.
7. Heat the solution from step 6 to between 135-212 degrees Fahrenheit and maintain the solution within this temperature range for approximately 80 seconds.
8. Blend the heated solution from Step 7 at a high speed for 6-10 seconds while maintaining the heated solution between 135-212 degrees Fahrenheit.
9. Add Calcium Carbonate and blend at a high speed for approximately 10 seconds until the mixture thickens and froths while maintaining the heated mixture within a temperature range of between 135-212 degrees Fahrenheit.
10. Pour the heated mixture from Step 9 into the desired mold and cover while allowing the mixture to cool to room temperature.

A second embodiment of a preferred toothpaste composition formulation of the single servings 10 of toothpaste in preformed shapes includes the following ingredients:

EXAMPLE 2

| Ingredient | Percentage by Weight in the Composition | Alternative Ingredients |
|---|---|---|
| Konjac | 1-4% | Agar-agar, Alginates, Gelatin, Pectin, Xanthan |
| Tara Gum | 0.2-0.7% | Agar-agar, Alginates, Gum Arabic, Carrageenan, Celluloses, Gelatin, Gellan Gum, Guar Gum, Inulin, Konjac, Locust Bean Gum, Pectin, Tragacanth, Xanthan |
| Xanthan/Guar | 0.15-0.55% | Agar-agar, Alginates, Gum Arabic, Carrageenan, Celluloses, Gelatin, Inulin, Konjac, Locust Bean Gum, Pectin, Tara, Tragacanth, Xanthan |
| Polyethylene Glycol-3350 | 2.75-3.9% | Polyethylene glycol-12 and/or similar polyethylene glycols |
| Xylitol | 38-51.2% | Xylitol - powdered |
| Calcium Carbonate | 5.79-7.14% | Heavy PCC Precipitated Calcium Carbonate |
| *Stevia* | 0.01-0.45% | *Stevia* Extract |
| *Quillaja* | 1.02-2.1% | *Quillaja* Extract |
| Bioflavonoid | 0.02-0.04% | Liquid Bioflavonoid Extract |
| Water | 41-54% | Purified Water |

A preferred process for production of the second embodiment of the single servings 10 of toothpaste in preformed shapes includes the following steps:

1. Heat water to between 100-212 degrees Fahrenheit.
2. Gradually add Xylitol to the heated water and mix until completely dissolved and a clear solution remains.
3. Cool the solution to 40-85 degrees Fahrenheit.
4. In a high shear mixer at a low speed, add Liquid Bioflavonoid and Quillaja to cooled solution and mix until completely dissolved.
5. In a ribbon-type blender at medium speed, blend together Konjac, Tara Gum, Xanthan/Guar, and Polyethylene glycol until well blended.
6. In a shaft-type homogenizing blender at low speed or bottom-mounted liquefier, add the blended solids from Step 5 to the solution from Step 4 and mix until mostly dissolved.
7. Heat the solution from step 6 to between 135-212 degrees Fahrenheit and maintain the solution within this temperature range for between 80 seconds and 5 minutes.
8. Blend the heated solution from Step 7 at a high speed for 6-20 seconds while maintaining the heated solution between 135-212 degrees Fahrenheit.
9. Add Calcium Carbonate and blend at a high speed for 10-30 seconds until the mixture thickens and froths while maintaining the heated mixture within a temperature range of between 135-212 degrees Fahrenheit.
10. Pour the heated mixture from Step 9 into the desired mold and cover while allowing the mixture to cool to room temperature.

A third embodiment of a preferred toothpaste composition formulation of the single servings 10 of toothpaste in preformed shapes produces a foam toothpaste product suitable for single serving packaging as well as multi-serving packaging and includes the following ingredients:

EXAMPLE 3

| Ingredient | Percentage by Weight in the Composition | Alternative Ingredients |
|---|---|---|
| Konjac | 1-4% | Agar-agar, Alginates, Gelatin, Pectin, Xanthan |
| Tara Gum | 0.3-0.7% | Agar-agar, Alginates, Gum Arabic, Carrageenan, Celluloses, Gelatin, Gellan Gum, Guar Gum, Inulin, Konjac, Locust Bean Gum, Pectin, Tragacanth, Xanthan |

-continued

| Ingredient | Percentage by Weight in the Composition | Alternative Ingredients |
|---|---|---|
| Xanthan/Guar | 0.15-0.55% | Agar-agar, Alginates, Gum Arabic, Carrageenan, Celluloses, Gelatin, Inulin, Konjac, Locust Bean Gum, Pectin, Tara, Tragacanth, Xanthan |
| Polyethylene glycol-3350 | 2.75-3.9% | Polyethylene glycol-3350, Polyethylene glycol-12, and/or similar polyethylene glycols |
| Xylitol | 38-51.2% | Xylitol - powdered |
| Calcium Carbonate | 5.79-7.14% | Heavy PCC Precipitated Calcium Carbonate |
| *Stevia* | 0.01-0.45% | *Stevia* Extract |
| *Quillaja* | 1.02-2.1% | *Quillaja* Extract |
| Bioflavonoid | 0.02-0.04% | Liquid Bioflavonoid Extract |
| Water | 41-54% | Purified Water |

A preferred process for production of the third embodiment of the single servings 10 of toothpaste in preformed shapes includes the following steps:
1. Heat water to between 100-212 degrees Fahrenheit.
2. Gradually add Xylitol to the heated water and mix until completely dissolved and a clear solution remains.
3. Cool the solution to 40-85 degrees Fahrenheit.
4. In a high shear mixer at a low speed, add Liquid Bioflavonoid and Quillaja to cooled solution and mix until completely dissolved.
5. In a ribbon-type blender at medium speed, blend together Konjac, Tara Gum, Xanthan/Guar, and Polyethylene glycol until well blended.
6. In a shaft-type homogenizing blender at low speed or bottom-mounted liquefier, add the blended solids from Step 5 to the solution from Step 4 and mix until mostly dissolved.
7. Heat the solution from step 6 to between 135-212 degrees Fahrenheit and maintain the solution within this temperature range for between 80 seconds and 5 minutes.
8. Blend the heated solution from Step 7 at a high speed for 6-20 seconds while maintaining the heated solution between 135-212 degrees Fahrenheit.
9. Add Calcium Carbonate and blend at a high speed for 30-60 seconds until the mixture thickens and froths while maintaining the heated mixture within a temperature range of between 135-212 degrees Fahrenheit.
10. Pour the heated mixture from Step 9 into the desired mold and cover while allowing the mixture to cool to room temperature.

The flavor of each of the compositions of the single servings 10 may be altered by the addition of natural and/or artificial flavorants for enhancing the taste and smell sensations when brushing one's teeth.

Figure 2:
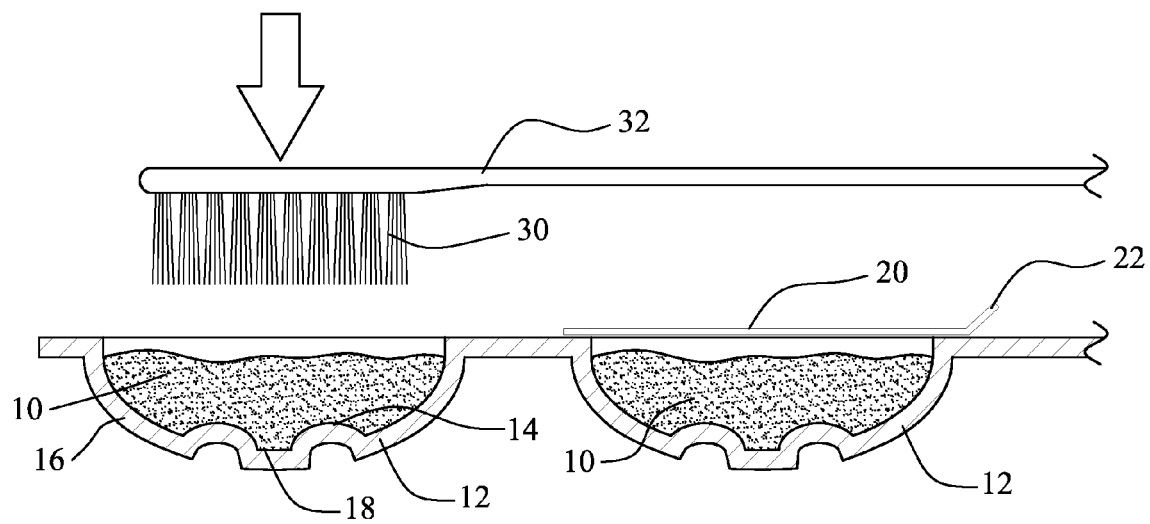
FIG. 2 is a side view, shown in partial cross-section, illustrating the bristles of a toothbrush approaching a compartment of the package for adhering to a single serving of toothpaste.
Figure 3:
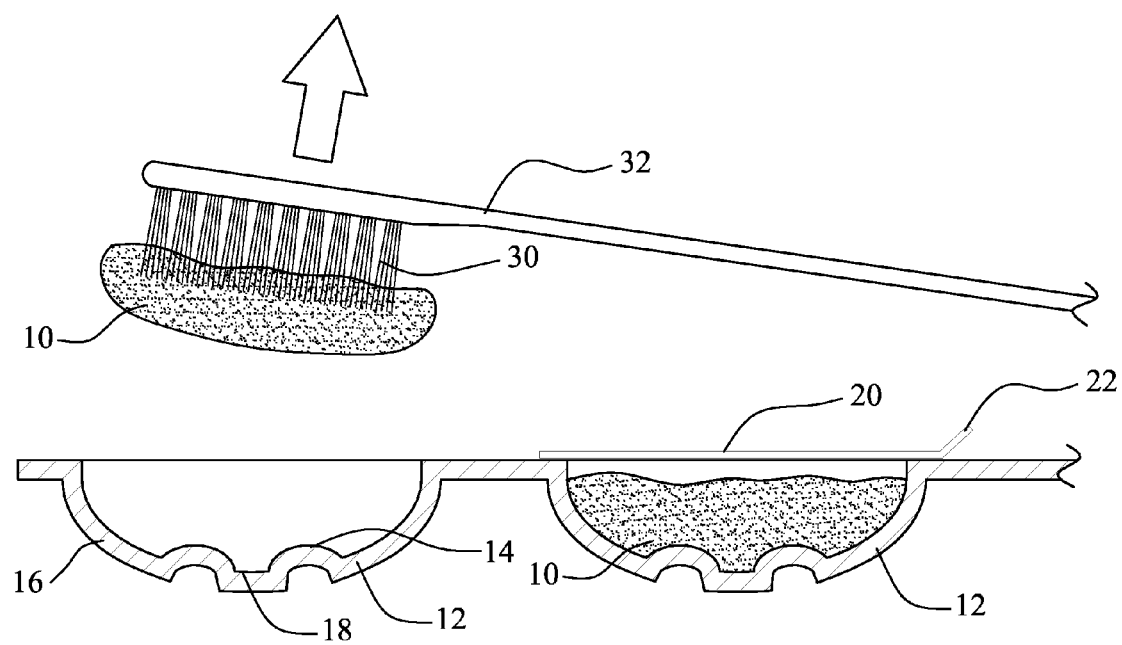
FIG. 3 is a side view, shown in partial cross-section, illustrating a single serving of toothpaste removed from the package compartment and clinging to the bristles of a toothbrush as the toothbrush is lifted away from the package.

The compositions of the single servings 10 of toothpaste are formulated to maintain the shape of a mold or the package compartments 12 after the toothpaste composition cools to room temperature. Referring to FIGS. 1-3, the single servings 10 of toothpaste are preferably stored in open-top compartments 12 of a package having protrusions 14 extending from portions of the sidewalls 16 and bottom wall 18 of the compartment 12. The protrusions 14 assist in preventing a single serving 10 of toothpaste from adhering to the sidewalls 16 and bottom wall 18 of the compartment 12 by limiting the surface area in contact with the single serving 10 of toothpaste. Each compartment 12 includes a removable pull tab 20 for covering the open top of the compartment 12 for securing the single serving 10 of toothpaste within the compartment 12 prior to use.

Referring to FIGS. 2 and 3, to use a single serving 10 of toothpaste, a user removes the protective film 20 by pulling the corresponding pull tab 22 to expose a single serving 10 of toothpaste within the compartment 12. The user subsequently presses the bristles 30 of a toothbrush 32 against the single serving 10 of toothpaste. The single serving 10 of toothpaste adheres (i.e., clings) to the bristles 30 and may then be lifted outwards of the compartment 12 and into the user's mouth for brushing.

While the present invention has been shown and described in accordance with several preferred and practical embodiments thereof, it is recognized that departures from the instant disclosure are fully contemplated within the spirit and scope of the invention as defined in the following claims and as interpreted under the Doctrine of Equivalents.

What is claimed is:
1. A toothpaste composition comprising:
a first gum in an amount of between 1.0% and 4.0% by weight of the composition, and said first gum comprising konjac gum;
a second gum in an amount of between 0.1% and 0.7% by weight of the composition, and said second gum comprising tara gum;
a third gum in an amount of between 0.15% and 0.55% by weight of the composition, and said third gum comprising a blend of xanthan and guar gums;
polyethylene glycol-3350 in an amount of between 2.75% and 3.9% by weight of the composition;
xylitol in an amount of between 38.0% and 51.2% by weight of the composition;
calcium carbonate in an amount of between 5.79% and 7.14% by weight of the composition; and
water in an amount of between 41.0% and 54.0% by weight of the composition.
2. The toothpaste composition as recited in claim 1 further comprising:
stevia in an amount of between 0.01% and 0.45% by weight of the composition.
3. The toothpaste composition as recited in claim 1 further comprising:
bioflavonoid in an amount of between 0.02% and 0.04% by weight of the composition.

\* \* \* \* \*